(12) United States Patent
Shlomovitz et al.

(10) Patent No.: US 7,462,159 B1
(45) Date of Patent: Dec. 9, 2008

(54) KNEE-ANKLE-FOOT ORTHOTIC DEVICE

(76) Inventors: Tal Shlomovitz, 38 Hameri St., Givataim (IL) 53330; Ronny Shelly, 16 Simtat Hakishon St., Ganey-Tikva (IL) 55900

( * ) Notice: Subject to any disclaimer, the term of this patent is extended or adjusted under 35 U.S.C. 154(b) by 0 days.

(21) Appl. No.: 11/782,136

(22) Filed: Jul. 24, 2007

(51) Int. Cl.
*A61F 5/00* (2006.01)
(52) U.S. Cl. ............................... 602/16; 602/23; 602/27
(58) Field of Classification Search ............ 602/5, 602/16, 23, 27; 128/882
See application file for complete search history.

(56) References Cited

U.S. PATENT DOCUMENTS

| | | | |
|---|---|---|---|
| 2,943,622 A | | 7/1960 | Nelson |
| 4,451,939 A | | 6/1984 | Thompson |
| 4,456,003 A | * | 6/1984 | Allard et al. .................. 602/16 |
| 4,632,096 A | * | 12/1986 | Harris ......................... 602/16 |
| 4,776,326 A | * | 10/1988 | Young et al. .................. 602/16 |
| 5,328,444 A | * | 7/1994 | Whiteside ..................... 602/16 |
| 5,776,086 A | | 7/1998 | Pansiera |
| 5,899,869 A | | 5/1999 | Barrack, Jr. et al. |
| 6,159,248 A | | 12/2000 | Gramnas |
| 6,517,503 B1 | | 2/2003 | Naft et al. |
| 6,635,024 B2 | | 10/2003 | Hatton et al. |
| 6,770,045 B2 | | 8/2004 | Naft et al. |
| 6,690,175 B2 | | 11/2005 | Myers |
| 2002/0169402 A1 | | 11/2002 | Hatton et al. |
| 2002/0183673 A1 | | 12/2002 | Naft et al. |
| 2004/0049291 A1 | | 3/2004 | Deharde et al. |
| 2006/0211966 A1 | | 9/2006 | Hatton et al. |

* cited by examiner

*Primary Examiner*—Michael A. Brown
(74) *Attorney, Agent, or Firm*—Antoinette M. Tease

(57) ABSTRACT

An ankle-foot orthotic device comprising a main hinge assembly; ankle hinge assembly; two ankle pivot points; foot plate; lower leg housing member; upper leg housing member; and cable; wherein the main hinge assembly comprises a first elongated member, a second elongated member, and a locking lever; wherein the first elongated member comprises a gear and a unidirectional bearing; wherein a spring maintains the locking lever in an engaged position in which the teeth of the locking lever engage with the teeth on the gear, thereby maintaining the gear in a stationary position; wherein when the cable is pulled taught, the spring of the locking lever is compressed, and the locking lever is disengaged from the gear; wherein the ankle hinge assembly is situated above the heel portion of the foot plate; and wherein the cable connects the ankle hinge assembly to the locking lever.

9 Claims, 14 Drawing Sheets ized gait. This feature ensures knee joint stability prior to heel contact and provides added safety, security and stability for individuals who fail to reach full knee extension.

KNEE-ANKLE-FOOT ORTHOTIC DEVICE

BACKGROUND OF THE INVENTION

1. Field of the Invention

The present invention relates generally to the field of assisted walking for the rehabilitation of handicapped persons, and more particularly, to a knee-ankle-foot orthotic device designed to enable safe ambulation in patients suffering from weakness or lack of control of the knee joint.

2. Description of the Related Art

Orthotic devices are often provided for patients afflicted with polio, spinal cord injury, cerebrovascular accidents (e.g., stroke) and multiple sclerosis. In addition, patients suffering from nerve root injuries, other neurological or muscular diseases, or who experience secondary loss of control of the knee may require the use of an orthotic device. The problem that these orthotic devices attempt to address is the lack of knee control during the weight-bearing stages of the gait cycle.

Numerous attempts for enabling patients a safe ambulation have been provided, though none with the functionality of the present invention. For example, the UTX® Swing Knee Ankle Foot Orthosis manufactured by Becker Orthopedic of Troy, Mich., is a device intended to stabilize the knee during the stance phase of gait but enable knee flexion during the swing phase. At the end of the swing phase, as the knee reaches full extension, a ratchet engages to stabilize the knee. At the end of the stance phase, as the ankle dorsiflexes, a cable linkage is used to unlock the knee joint and allow it to move freely.

The Free-Walk design manufactured by Otto Bock of Duderstadt, Germany and Minneapolis, Minn. creates a natural gait cycle by locking during the stance phase and unlocking during the swing phase. The automatic lock is initiated by knee extension and is only released to swing freely when a knee extension moment occurs simultaneously with ankle dorsiflexion in the terminal stance.

The Swing Phase Lock (SPL) manufactured by BASKO of Amsterdam, Netherlands is yet another existing knee hinge orthosis system. This system automatically unlocks in order to allow knee flexion, and it locks before heel contact takes place. The SPL hinge system can only unlock when there is no flexion moment or strain of bending put on the hinge.

U.S. Pat. No. 4,632,096 (Harris, 1986) is an example of a prior art orthotic system for the leg. This system releases automatically upon a pre-selected dorsiflexion of the ankle followed by a pre-selected flexion of the ankle. The orthotic devices provided with a lock hinge that spans the pivoting means and locks the upper member and lower member when the leg approaches extension during a gait cycle.

Examples of other prior art knee braces and/or orthotic joints include U.S. Pat. Nos. 6,960,175 (Myers, 2005); 6,770,045 (Naft et al., 2004); U.S. Pat. No. 6,635,024 (Hatton et al., 2003); U.S. Pat. No. 6,517,503 (Naft et al., 2003); U.S. Pat. No. 6,159,248 (Grammas, 2000); U.S. Pat. No. 5,899,869 (Barrack, Jr., et al., 1999); U.S. Pat. No. 5,776,086 (Pansiera, 1998); U.S. Pat. No. 4,451,939 (Thompson, 1984); U.S. Pat. No. 2,943,622 (Nelson, 1960); U.S. Patent Application Pub. No. 20060211966 (Hatton et al.); U.S. Patent Application Pub. No. 2004/0049291 (Deharde et al.); U.S. Patent Application Pub. No. 2002/0183673 (Naft et al.); and U.S. Patent Application No. 20020269402 (Hatton et al.).

In contrast to prior art devices, the present invention utilizes a low-profile cabling system that will automatically unlock at terminal stance, to allow for free knee flexion, and then reengage at mid-swing, permitting only knee extension (and not knee flexion). This feature ensures knee joint stabil-

BRIEF SUMMARY OF THE INVENTION

The present invention is an ankle-foot orthotic device comprising a main hinge assembly; an ankle hinge assembly; two ankle pivot points; a foot plate; a lower leg housing member; an upper leg housing member; and a cable; wherein the main hinge assembly comprises a first elongated member and a second elongated member; wherein the first elongated member is fixedly attached to the lower leg housing member and the second elongated member is fixedly attached to the upper leg housing member; wherein the first elongated member comprises a gear and a unidirectional bearing; wherein the gear comprises teeth; wherein the unidirectional bearing is situated inside of the gear; wherein the main hinge assembly further comprises a locking lever; wherein the locking lever comprises teeth and a spring; wherein the spring maintains the locking lever in an engaged position unless the spring is compressed; wherein when the locking lever is in an engaged position, the teeth of the locking lever engage with the teeth on the gear, thereby maintaining the gear in a stationary position; wherein when the gear is maintained in a stationary position, the unidirectional bearing only allows the first and second elongated members to move in one direction in relation to one another, that direction corresponding to the extension of a patient's leg at the knee; wherein when the cable is pulled taught, the spring of the locking lever is compressed, and the locking lever is disengaged from the gear; wherein when the locking lever is disengaged from the gear, the gear allows the first and second elongated members to move in two directions in relation to one another, those two directions corresponding to the flexion and extension of a patient's leg at the knee; wherein the foot plate comprises a heel portion; wherein the ankle hinge assembly is situated above the heel portion of the foot plate; and wherein the cable connects the ankle hinge assembly to the locking lever.

In a preferred embodiment, when a patient wearing the device dorsiflexes his ankle, the cable is pulled taught, and the locking lever is disengaged from the gear, thereby allowing the patient to either flex or extend his leg at the knee. In a preferred embodiment, when the patient's ankle is no longer dorsiflexed, the locking lever engages with the gear, thereby allowing the patient to extend his leg at the knee but not to flex it.

In a preferred embodiment, the foot plate, lower leg housing member and upper leg housing member are all open along the front and are comprised of a durable plastic material that is able to slightly bend.

In a preferred embodiment, the device comprises one or two main hinge assemblies; wherein the ankle hinge assembly comprises a first and second aperture; wherein for each main hinge assembly on the device, a single cable extends through one of the apertures on the ankle hinge assembly; wherein each cable comprises a stop that prevents the cable from exiting the ankle hinge assembly when the cable is pulled taught; and wherein the cable is fixedly attached to the locking lever.

In a preferred embodiment, each ankle pivot point comprises a plastic or metal hinge that joins the foot plate to the lower leg housing member at a position corresponding roughly to a patient's ankle when the patient is wearing the device.

In a preferred embodiment, the first and second elongated members are joined together with a main screw and a threaded shaft; wherein the main screw fits into the threaded shaft; and wherein the shaft extends through the center of the unidirectional bearing.

In a preferred embodiment, the second elongated member comprises two circular arms that form a channel into which the first elongated member is inserted. Preferably, the main hinge assembly further comprises a washer that lies between the gear and one of the circular arms of the second elongated member.

REFERENCE NUMBERS

Figure 1:
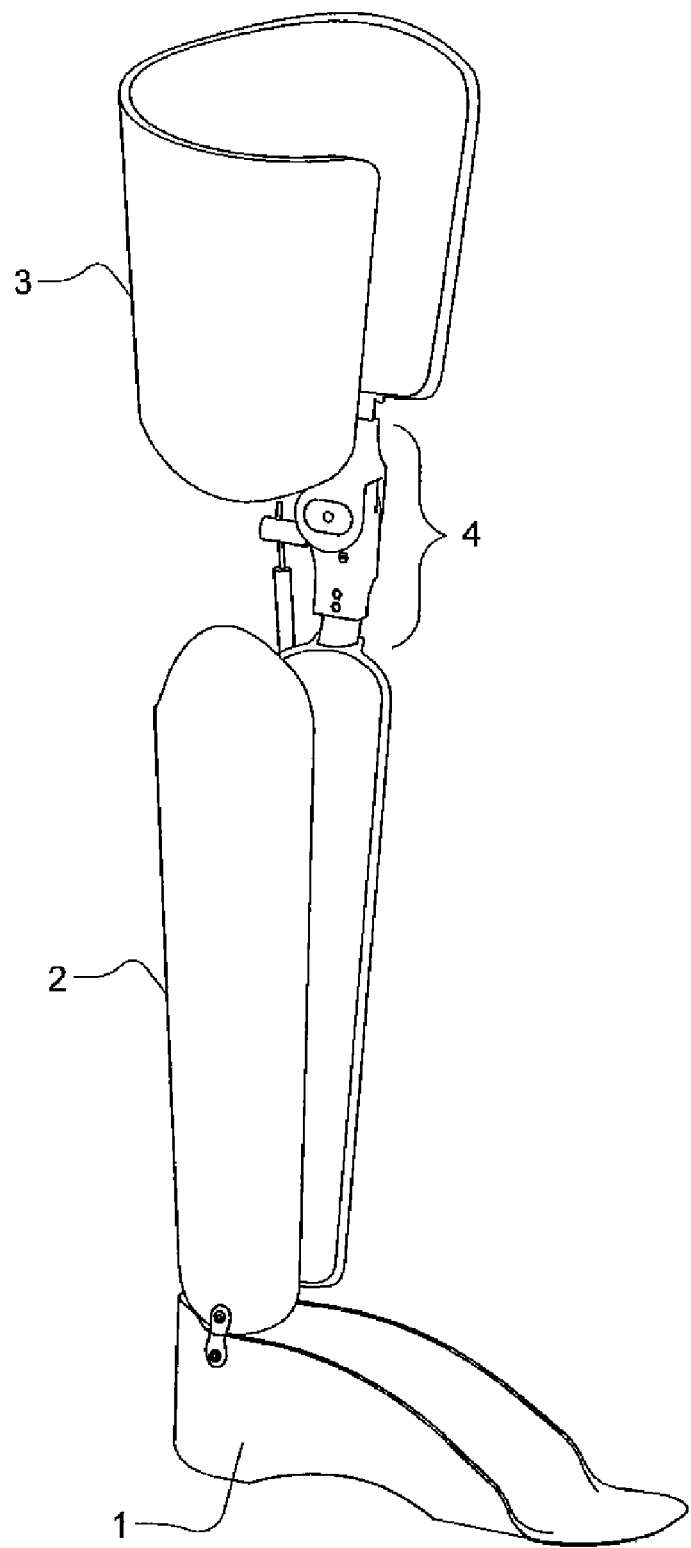
FIG. 1 is a front perspective view of the present invention with the device in a fully extended position.

1 Foot plate
2 Lower leg housing member
3 Upper leg housing member
4 Main hinge assembly
5 First elongated member
6 Second elongated member
7 Ankle hinge assembly
8 Cable
9 Plastic tubing
10 Locking lever
11 Pivot point
12 Screw
13 Main screw
14 Threaded shaft
15 Gear
16 Circular arms (of second elongated member)
17 Washer
18 Unidirectional bearing
19 Teeth (on locking lever)
20 Teeth (on gear)
21 Spring
22 Aperture (for cable)
23 Stop
24 Aperture (for screw)

DETAILED DESCRIPTION OF INVENTION

The present invention is a self-locking and self-releasing knee-ankle-foot orthotic device that enables and/or improves ambulation for handicapped persons without requiring the leg of the patient to be locked in extension during the entire gait cycle. Furthermore, the main hinge assembly of the present invention reengages and is locked prior to heel strike. This feature makes the device inherently safer than prior art devices because the knee locking mechanism is engaged prior to the foot hitting the ground, even when the knee is bent.

The present invention comprises a main hinge assembly that allows the patient to extend but not flex at the knee until the ankle is dorsiflexed, at which point the main hinge assembly automatically unlocks, and the leg is allowed to flex until maximum knee flexion is achieved. When the ankle resumes a non-dorsiflexed position, the joint mechanism automatically locks again, and the patient may again extend but not flex his leg at the knee. In this manner, the patient's knee is stabilized, and normal gait may be approximated.

In addition to stabilizing the patient during ambulation and allowing the patient to approximate a normal gait, the present invention has been designed to be comfortable to wear and highly resistant to wear and tear. The present invention is described in greater detail with reference to FIGS. 1-14.

FIG. 1 is a front perspective view of the present invention with the device in a fully extended position. As shown in this figure, the present invention comprises a foot plate 1, a lower leg housing member 2, an upper leg housing member 3, and a main hinge assembly 4. The foot plate 1, lower leg housing member 2, and upper leg housing member 3 are preferably attached to the patient's leg with straps (not shown). The device may comprise one or two main hinge assemblies 4. In FIGS. 1-6, the present invention is shown with only one main hinge assembly 4 on one side of the leg, but there could be a main hinge assembly 4 on either side of the leg.

The lower and upper leg housing members 2, 3 are all open along the front and are preferably comprised of a durable plastic material that is able to slightly bend in order to be comfortably accommodated to the leg of a patient and to assist in the donning and doffing of the device.

Figure 2:
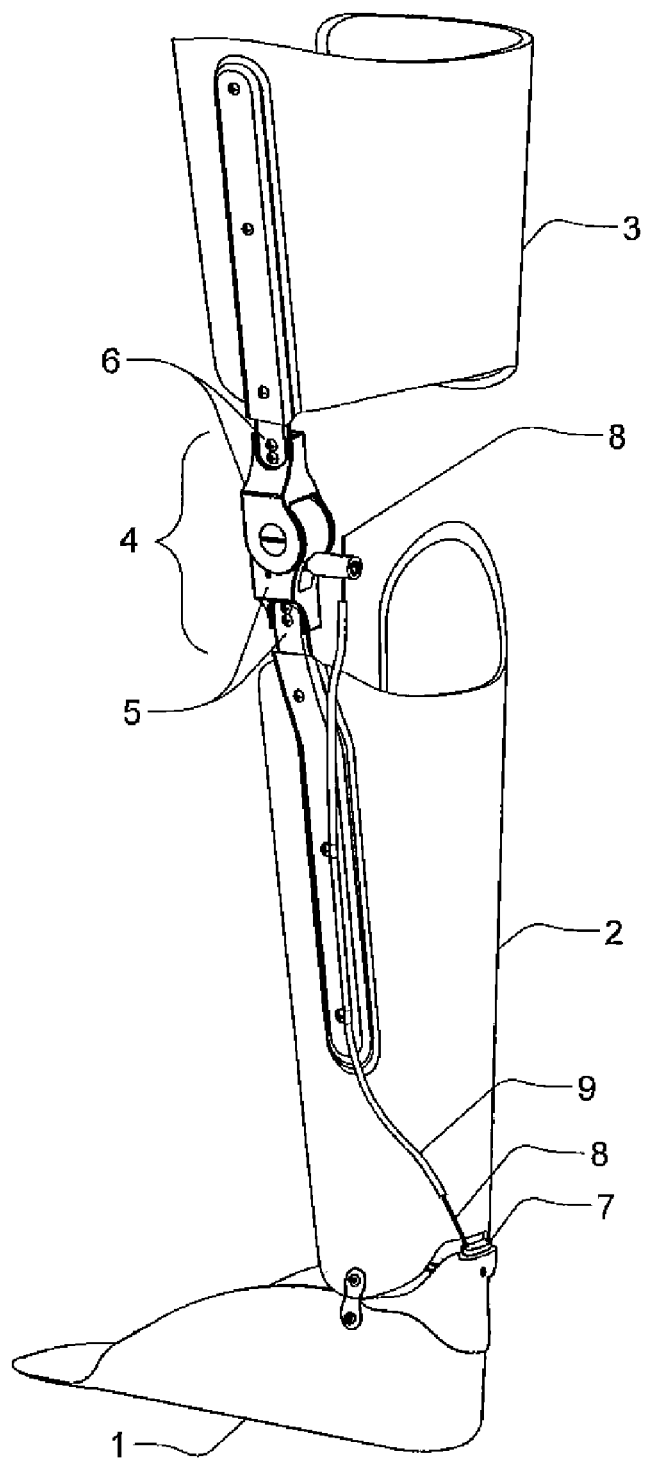
FIG. 2 is a rear perspective view of the present invention with the device in a fully extended position.

FIG. 2 is a rear perspective view of the present invention with the device in a fully extended position. This figure shows the foot plate 1, the lower leg housing member 2, the upper leg housing member 3, and the main hinge assembly 4. The main hinge assembly comprises a first elongated member 5 and a second elongated member 6. Together, the first and second elongated members 5, 6 form the main hinge assembly 4. An ankle hinge assembly 7 is located just above the heel portion of the foot plate 1. The ankle hinge assembly is preferably inserted into the foot plate 1 just above the heel portion. The ankle hinge assembly is shown in greater detail in FIG. 15.

A cable 8 connects the ankle hinge assembly 7 to the main hinge assembly 4. the cable is preferably covered with a protective plastic tubing 9 except where it enters the ankle hinge assembly 7 and the main hinge assembly 4.

Figure 3:
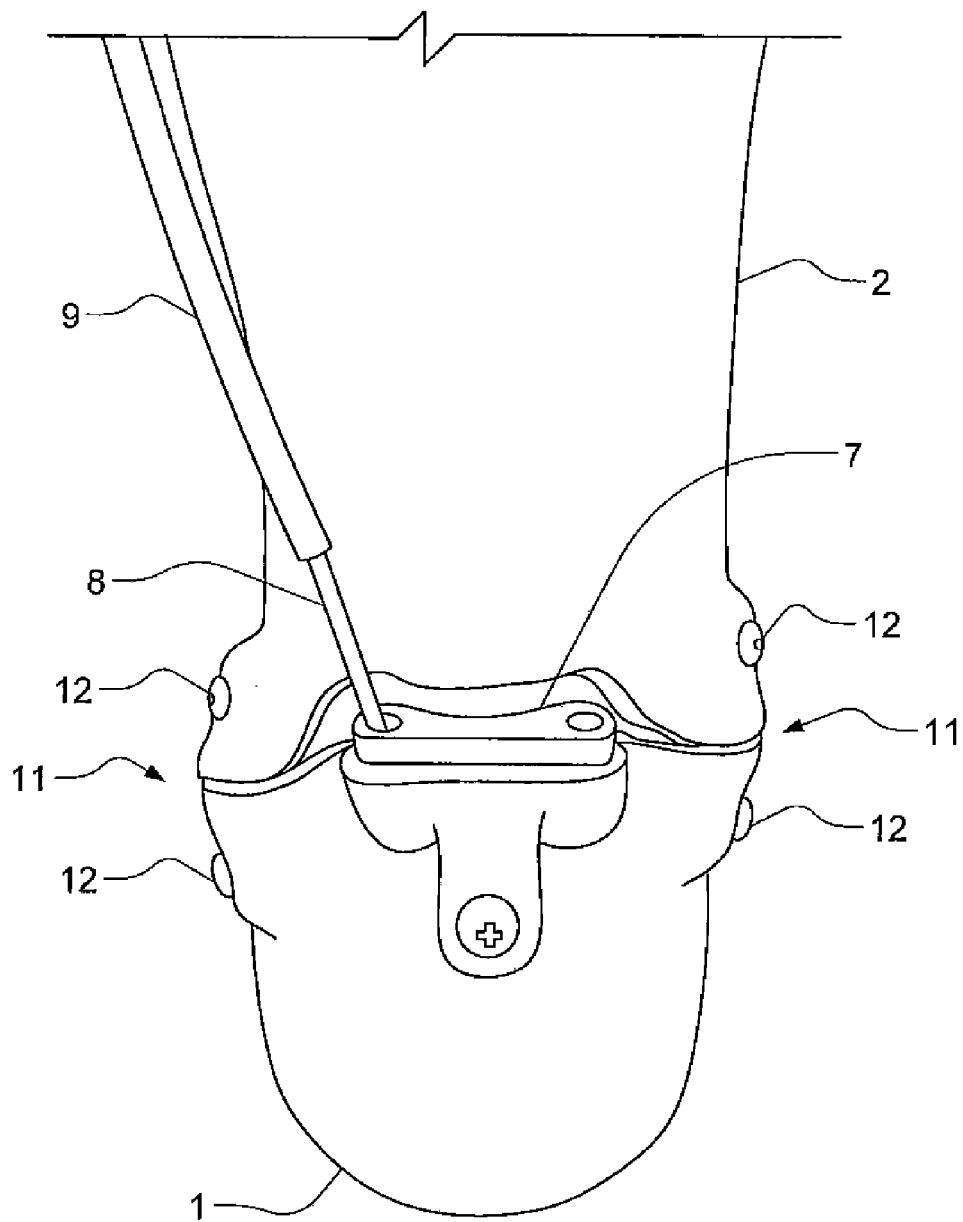
FIG. 3 is a rear view of foot plate and bottom portion of the lower leg housing member.

FIG. 3 is a rear view of the foot plate and bottom portion of the lower leg housing member. As shown in this figure, the cable 8 enters one side of the ankle hinge assembly 7. If there were two main hinge assemblies, one on either side of the brace, a cable 8 would enter the ankle hinge assembly 7 on both sides of the ankle hinge assembly. When the patient dorsiflexes his ankle, the cable is pulled taught inside the ankle hinge assembly (see FIG. 15), and the locking lever 10 (see FIG. 4) of the main hinge assembly 4 is pulled downward.

On either side of the foot plate 1 and lower leg assembly 2, roughly at the position of the patient's ankle, are two pivot points 11. In a preferred embodiment, the pivot points 11 are comprised of a plastic or metal hinge (not shown) that joins the foot plate 1 to the lower leg housing member 2 on either side of the device (at the pivot points 11). In the embodiment shown in FIG. 3, the pivot point 11 is a flexible plastic strip located inside of the foot plate 1 and lower leg housing 2 and attached to the foot plate 1 and lower leg housing member 2 with four screws 12, but the present invention is not limited to this particular embodiment.

Figure 4:
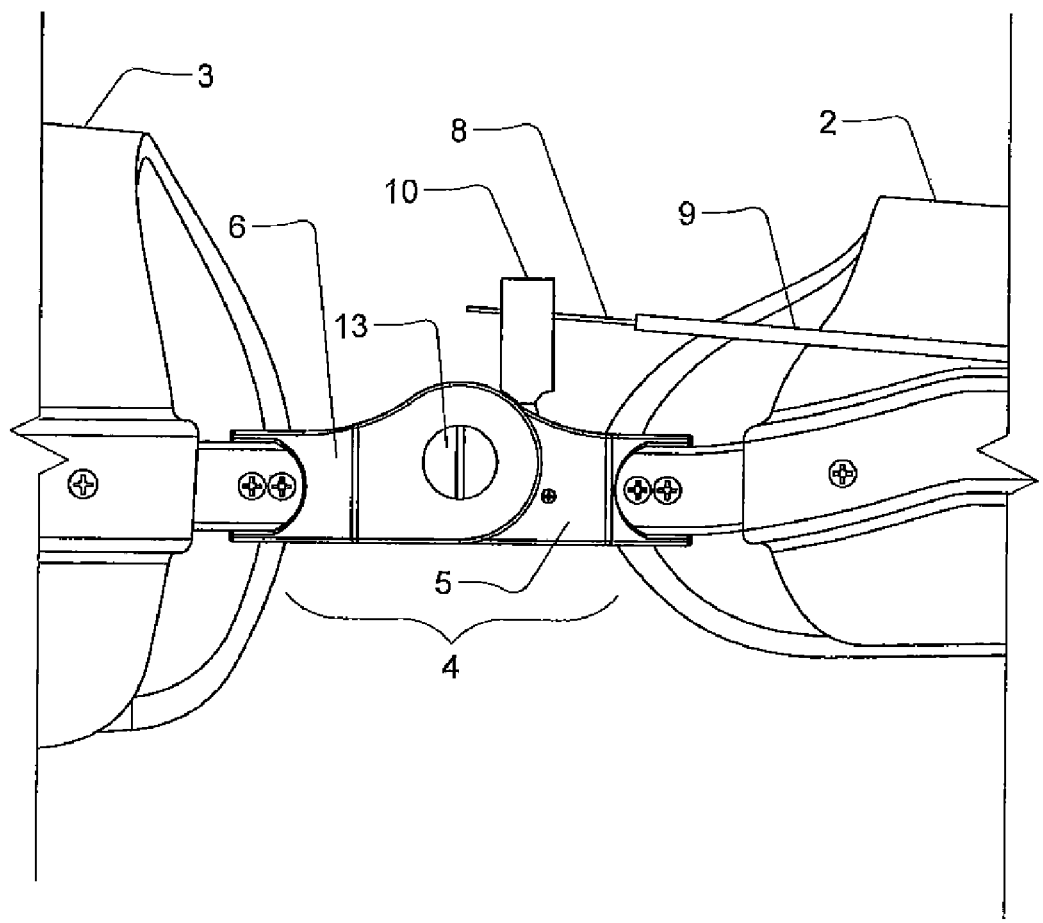
FIG. 4 is a detail view of the main hinge assembly of the present invention shown from the outer face of the main hinge assembly.

FIG. 4 is a detail view of the main hinge assembly of the present invention shown from the outer face of the main hinge assembly. The outer face of the main hinge assembly faces outward (away from the patient's knee) on the device. The main hinge assembly 4 comprises a first elongated member 5 and a second elongated member 6. The first and second elongated members 5, 6 are joined together with a main screw 13 and a shaft 14 (see FIG. 5). The main hinge assembly 4 further comprises a locking lever 10. The cable 8 is fixedly connected to the locking lever 10.

Figure 5:
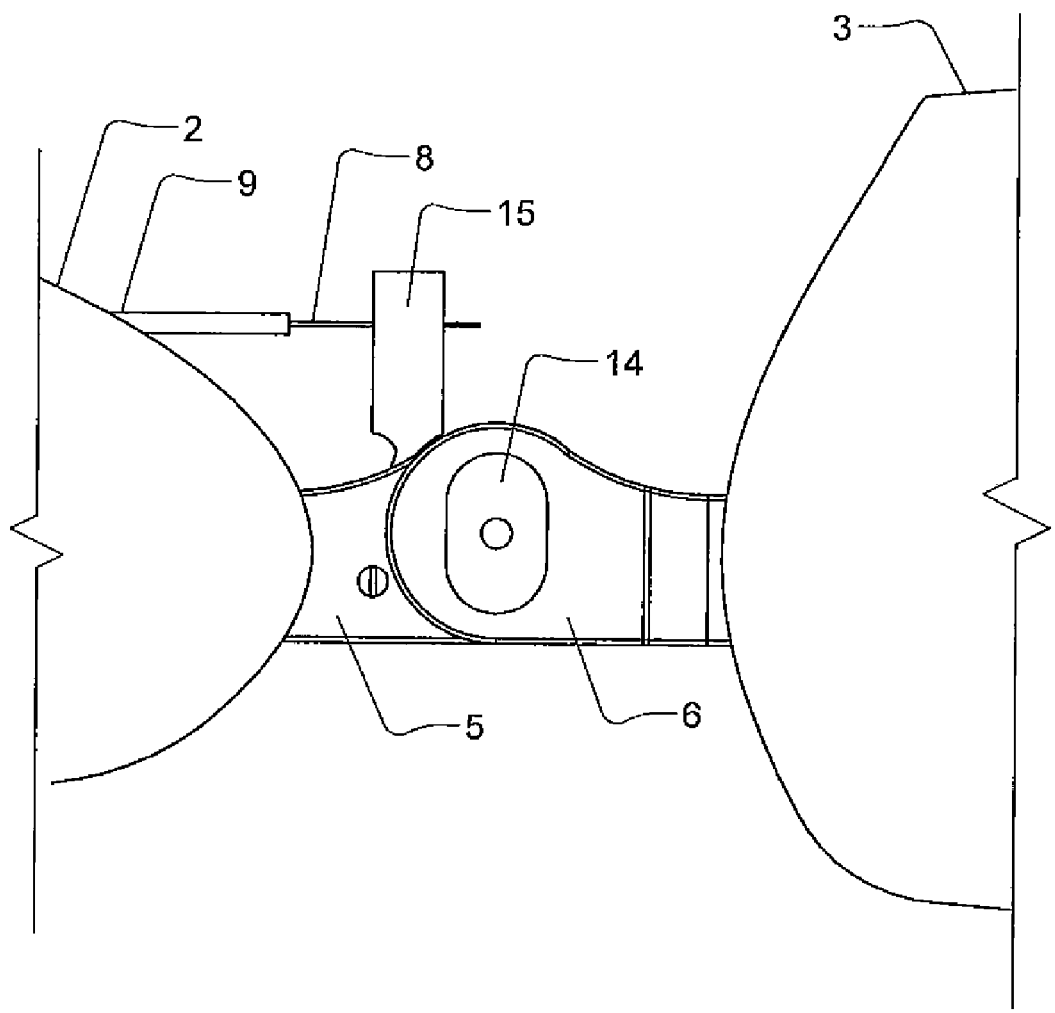
FIG. 5 is a detail view of the main hinge assembly of the present invention shown from the inner face of the main hinge assembly.

FIG. 5 is a detail view of the main hinge assembly of the present invention shown from the inner face of the main hinge assembly. The inner face of the main hinge assembly faces inward (toward the patient's knee) on the device. A threaded shaft 14 extends through the second elongated member 6, through a unidirectional bearing (see FIG. 10), through the first elongated member 5, and through the other side of the second elongated member 6 (this is shown more clearly in FIGS. 9 and 10). The main screw 13 screws into the threaded shaft 14.

Figure 6:
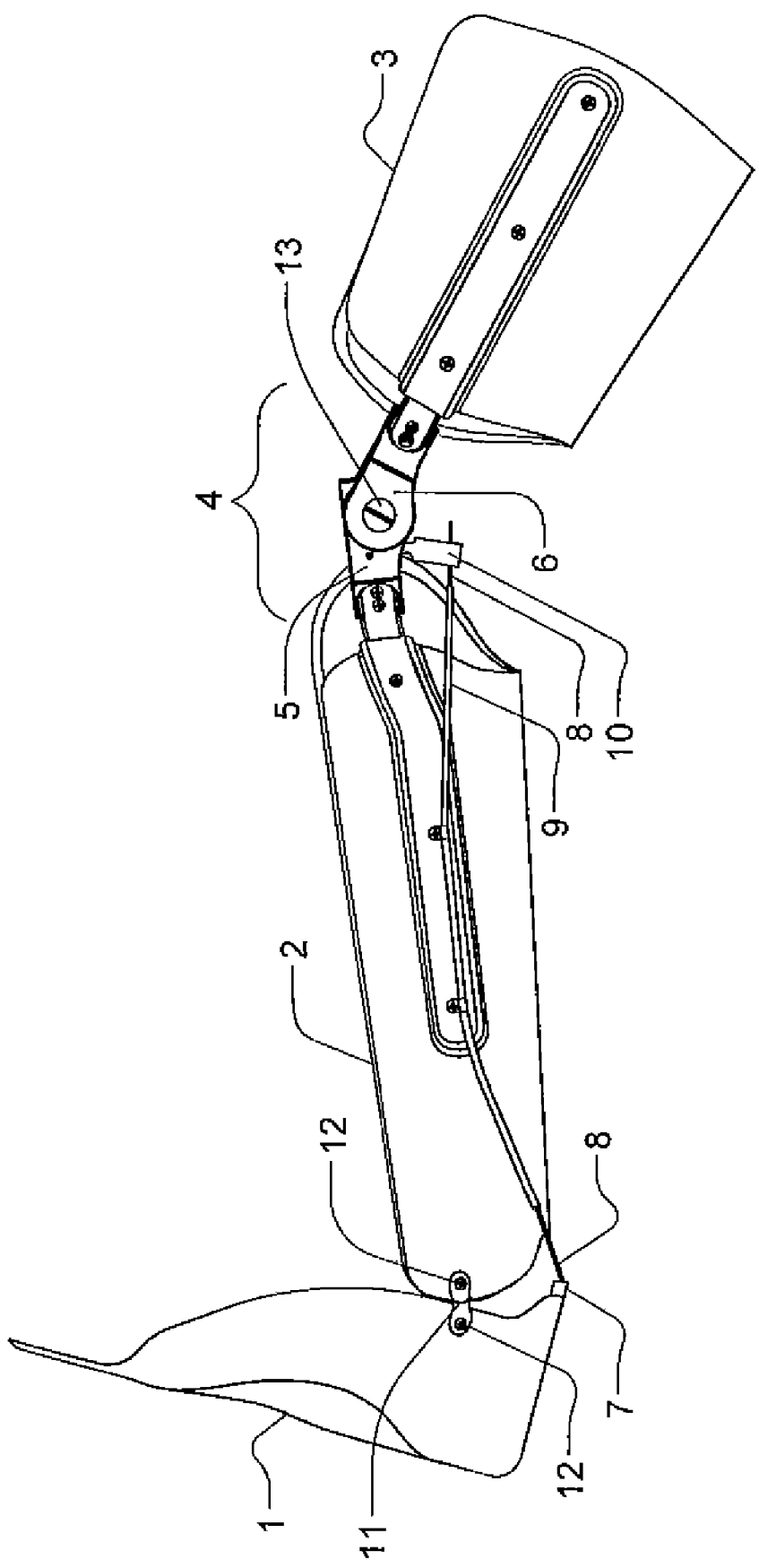
FIG. 6 is a side view of the present invention with the device in a flexed position.

FIG. 6 is a side view of the present invention with the device in a flexed position. This figure illustrates what happens when the patient dorsiflexes his or her ankle. In this position, the cable 8 is pulled taught inside the ankle hinge assembly 7, and the locking lever 10 is pulled downward. As shown in FIG. 11, when the locking lever 10 is pulled downward, it disengages from a gear 15 inside of the first elongated member 5, thereby allowing the knee to flex and the upper and lower leg housing members 2, 3 to move toward each other, as shown in FIG. 6. When the locking lever 10 is disengaged from the gear 15, the upper and lower leg housing members 2, 3 can also move away from each other; in other words, they can move freely in either direction. When the patient's ankle is not dorsiflexed and the locking lever is engaged with the gear 15 (see FIG. 10), the upper and lower leg housing members 2, 3 can only move in one direction, that is, away from each other (consistent with extension of the leg).

Figure 7:
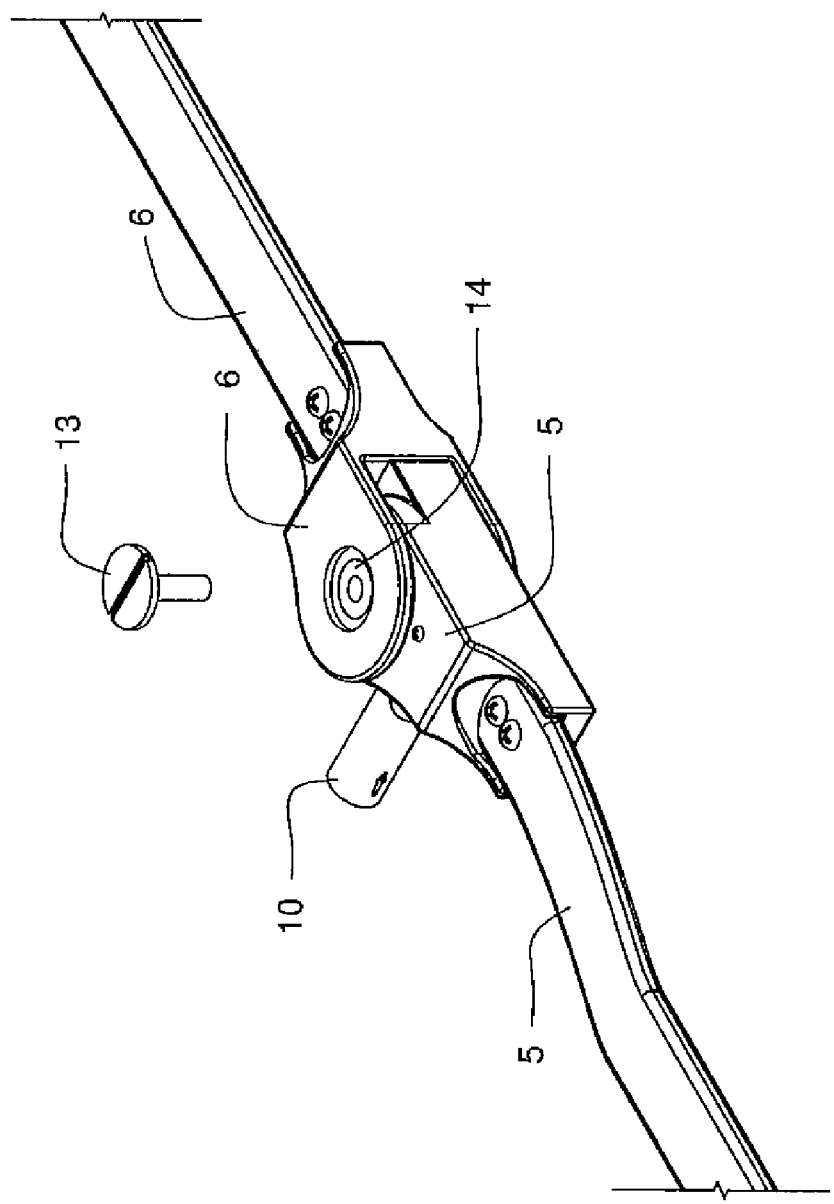
FIG. 7 is a perspective view of the main hinge assembly of the present invention shown from the outer face of the main hinge assembly without the upper and lower leg housing members, without the cable, and with the main screw removed.
Figure 8:
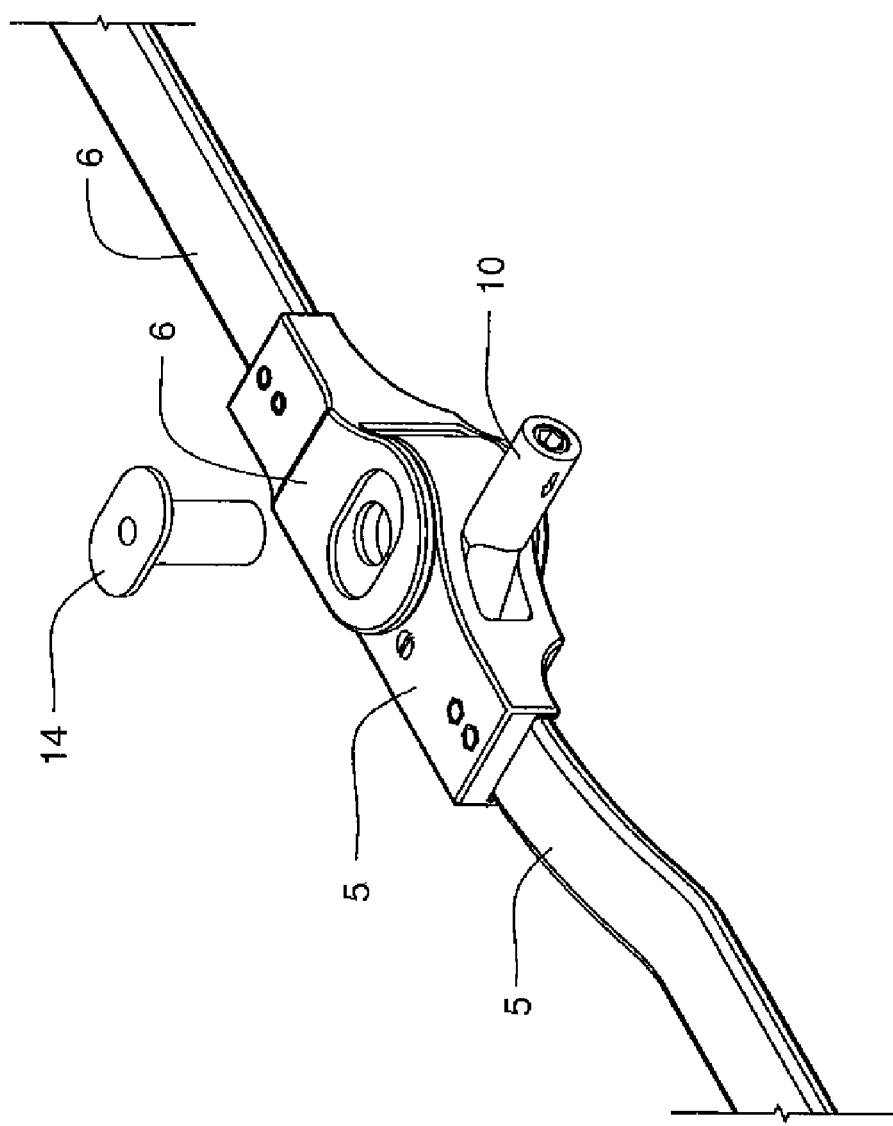
FIG. 8 is a perspective view of the main hinge assembly of the present invention shown from the inner face of the main hinge assembly without the upper and lower leg housing members and with the shaft removed.

FIGS. 7-10 illustrate how the main hinge assembly 4 of the present invention would be disassembled. The first step would be to remove the main screw 13. FIG. 7 is a perspective view of the main hinge assembly 4 shown from the outer face of the main hinge assembly without the upper and lower leg housing members 2, 3, without the cable 8, and with the main screw 13 removed. The next step would be to remove the threaded shaft 14. FIG. 8 is a perspective view of the main hinge assembly 4 shown from the inner face of the main hinge assembly without the upper and lower leg housing members 2, 3, without the cable 8, and with the threaded shaft 14 removed.

Figure 9:
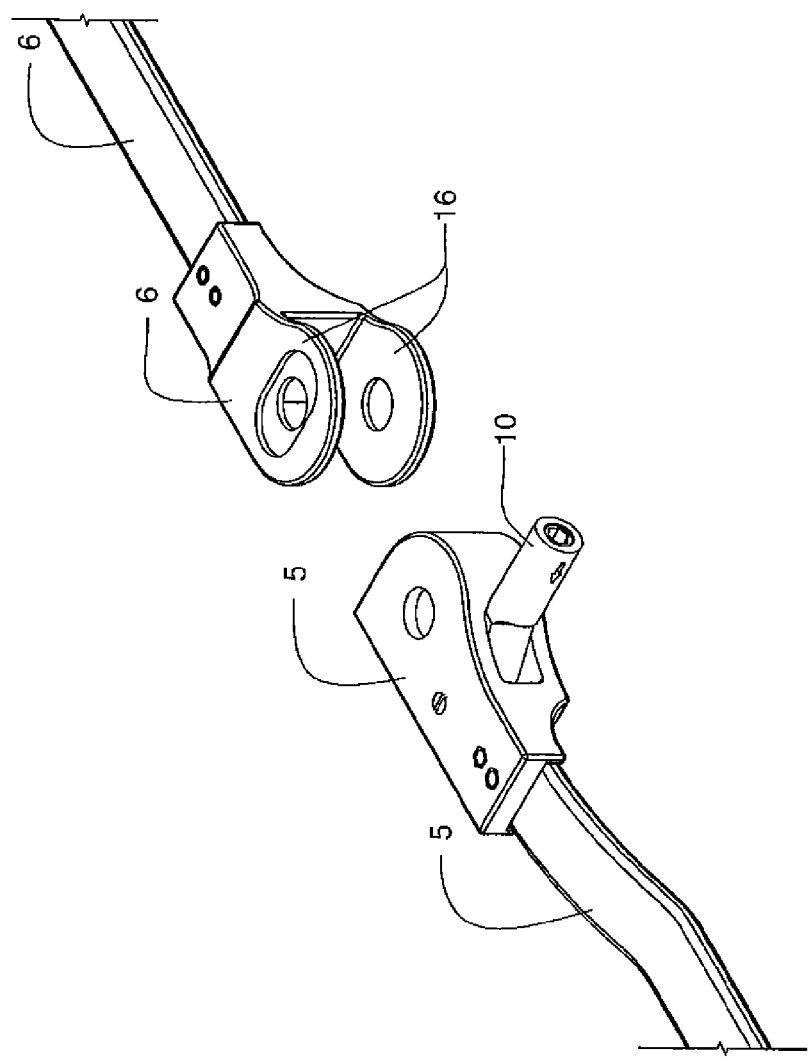
FIG. 9 is a perspective view of the main hinge assembly of the present invention shown from the inner face of the main hinge assembly with the first and second elongated members disconnected.

Next, the first and second elongated members 5, 6 would be pulled apart. FIG. 9 is a perspective view of the main hinge assembly 4 shown from the inner face of the main hinge assembly with the first and second elongated members 5, 6 disconnected. As shown in this figure, the second elongated member 6 comprises two circular arms that form a channel into which the first elongated member 5 is inserted.

Figure 10:
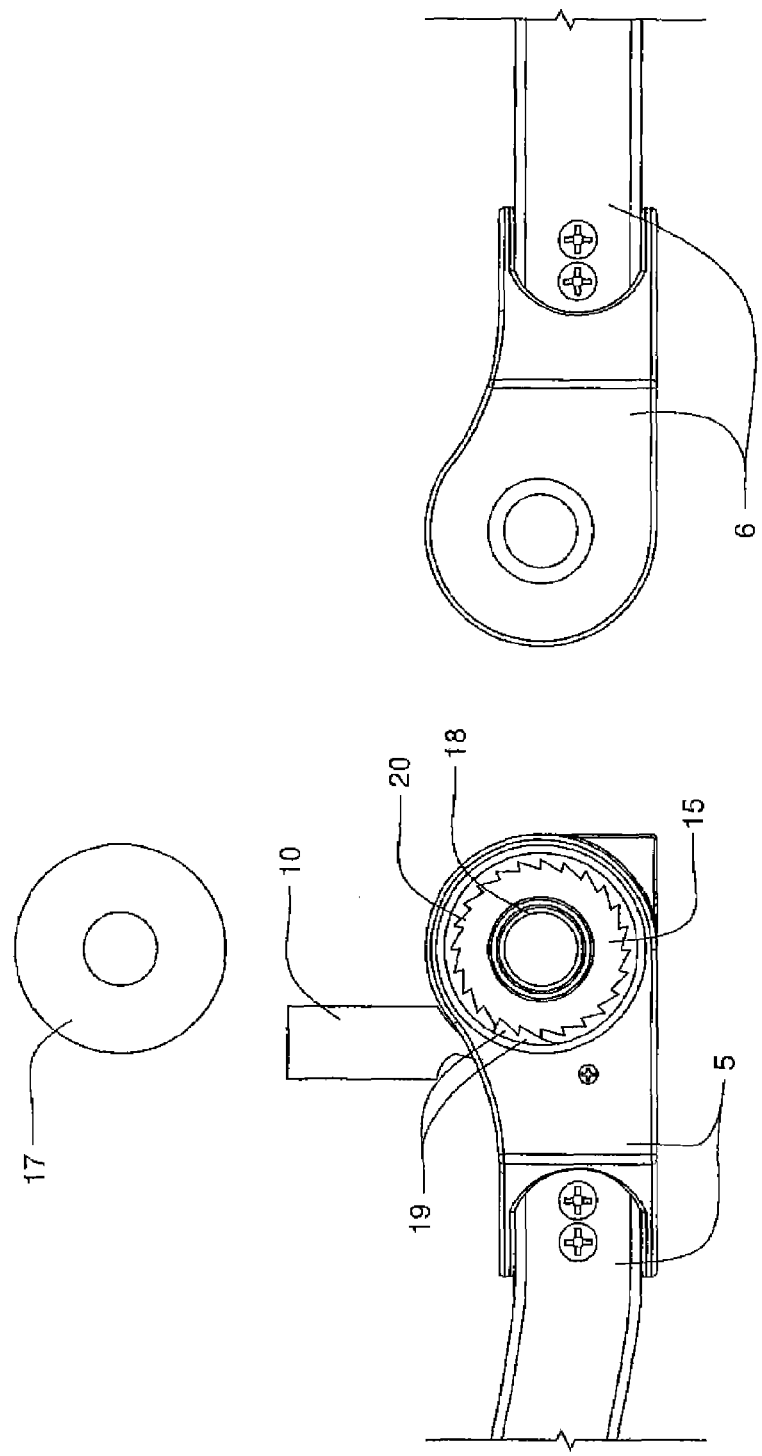
FIG. 10 is a detail view of the main hinge assembly of the present invention shown from the inner face of the main hinge assembly with the first and second elongated members disconnected and the gear exposed.
Figure 11:
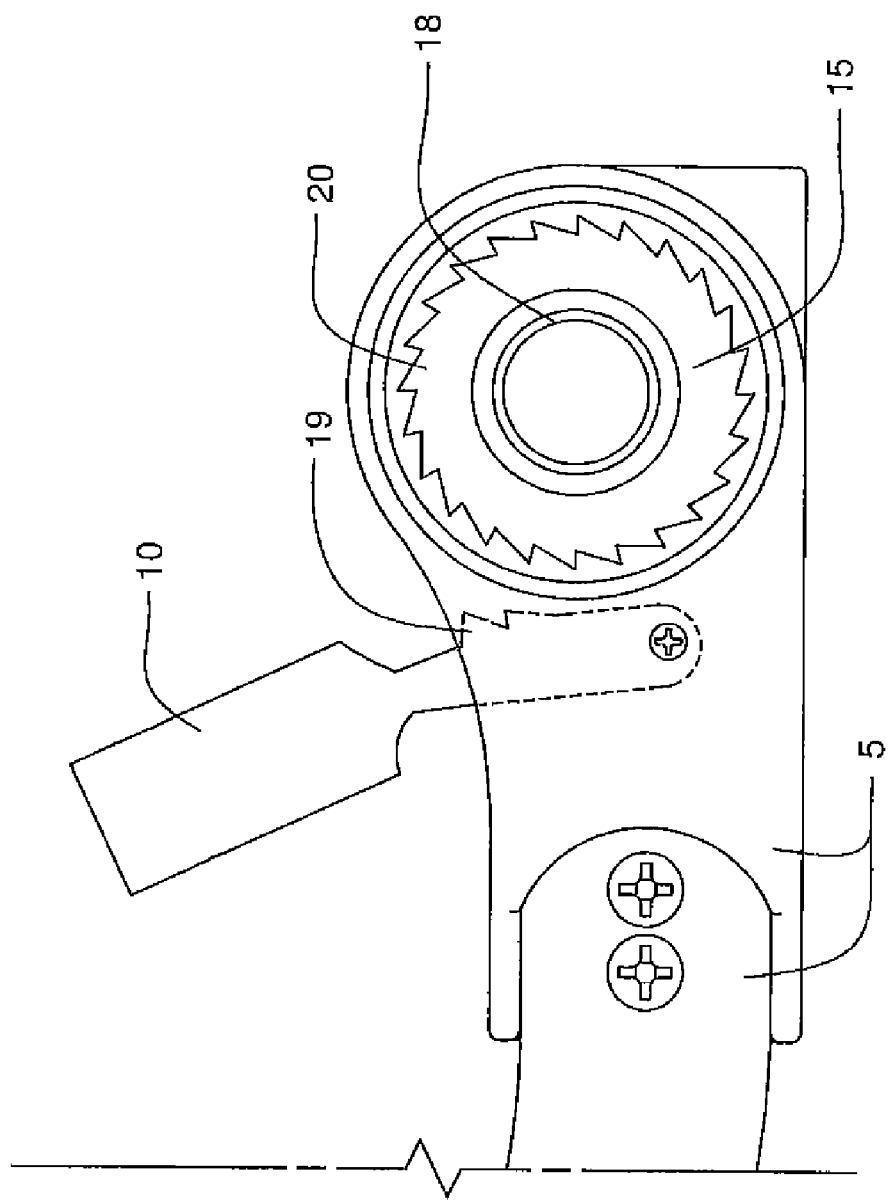
FIG. 11 is a detail view of the first elongated member with the gear exposed and the locking lever disengaged from the gear.

FIG. 10 shows the disassembled main hinge assembly 4 from the flip side of that shown in FIG. 9. FIG. 10 is a detail view of the main hinge assembly shown from the inner face of the main hinge assembly with the first and second elongated members disconnected and the gear 15 exposed. A washer 17 lies on top of the gear 15 and is set aside in this figure for clarity. A unidirectional bearing 18 is press fit inside of the gear 15. The locking lever 10 comprises teeth 19 that engage with the teeth 20 of the gear 15 when the patient's ankle is not dorsiflexed. When the teeth 19 of the locking lever 10 are engaged with the teeth 20 of the gear 15, the unidirectional bearing 18 only allows the first and second elongated members 5, 6 to move in one direction relative to each other (that is, in the direction that would result in extension of the leg). The lower leg housing member 2 is fixedly attached to the first elongated member 5, and the upper leg housing member 3 is fixedly attached to the second elongated member 6 (see FIG. 2).

FIG. 11 is a detail view of the first elongated member with the gear exposed and the locking lever disengaged from the gear. In this position, the gear functions as an external axis and allows the threaded shaft 14 (and therefore the second elongated member) to rotate in either direction relative. When the locking lever 10 is engaged with the gear 15 (as shown in FIG. 10), the gear is held stationary, and the unidirectional bearing functions as an internal axis, allowing the threaded shaft 14 to move only in a single direction (i.e., toward extension of the leg).

Figure 12:
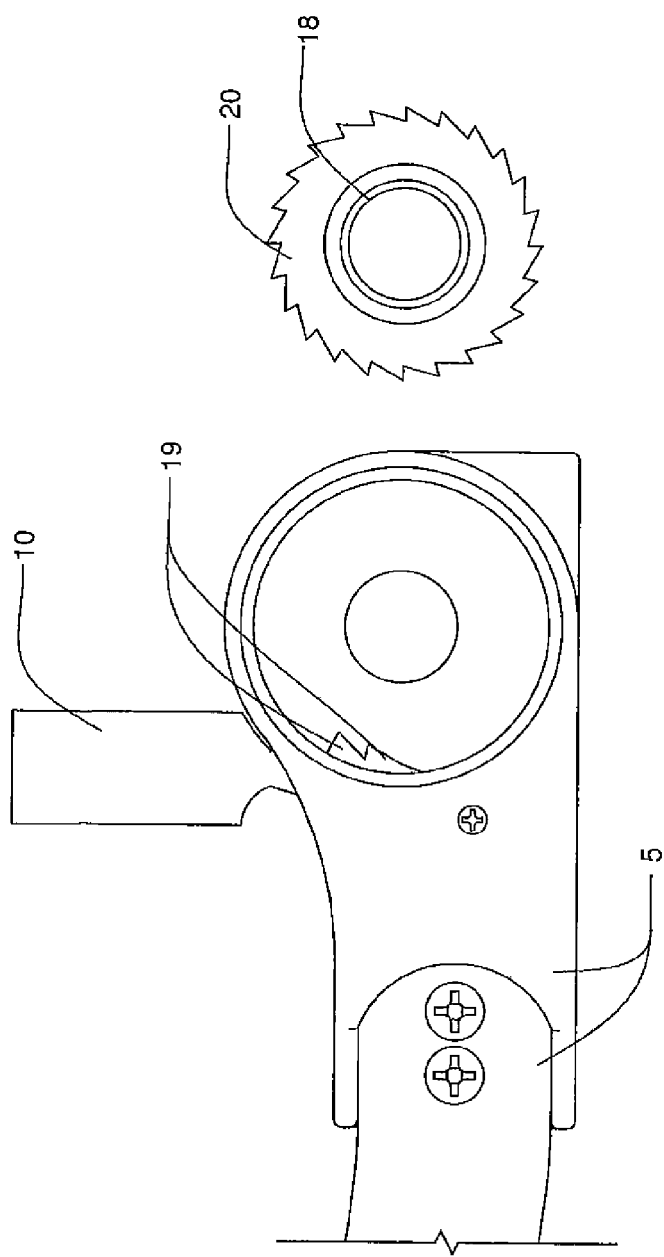
FIG. 12 is a detail view of the first elongated member with the gear removed and the locking lever in the same position as in FIG. 10.

FIG. 12 is a detail view of the first elongated member with the gear removed and the locking lever in the same position as in FIG. 10. The purpose of this figure is to show more clearly the teeth 19 of the locking lever 10.

Figure 13:
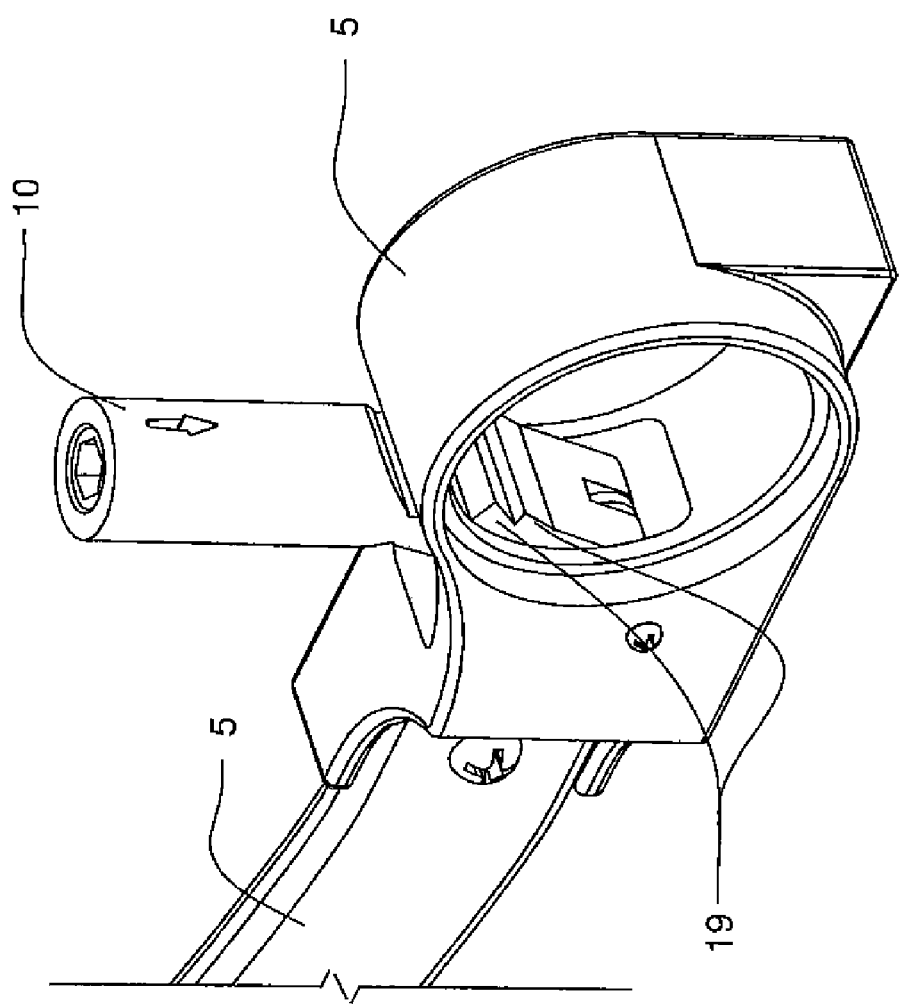
FIG. 13 is a perspective view of the first elongated member with the gear removed so that the spring that maintains the locking lever in the position shown in FIG. 12 is visible.

FIG. 13 is a perspective view of the first elongated member with the gear removed so that the spring that maintains the locking lever in the position shown in FIG. 12 is visible. When the patient's ankle is dorsiflexed, the cable 8 (not shown) is pulled taught and the locking lever is pulled downward (toward the lower leg housing member 2). When the locking lever 10 is pulled downward, a spring 21 directly underneath the locking lever is compressed. When the tension on the cable is released, the spring 21 returns the locking lever to its engaged position.

Figure 14:
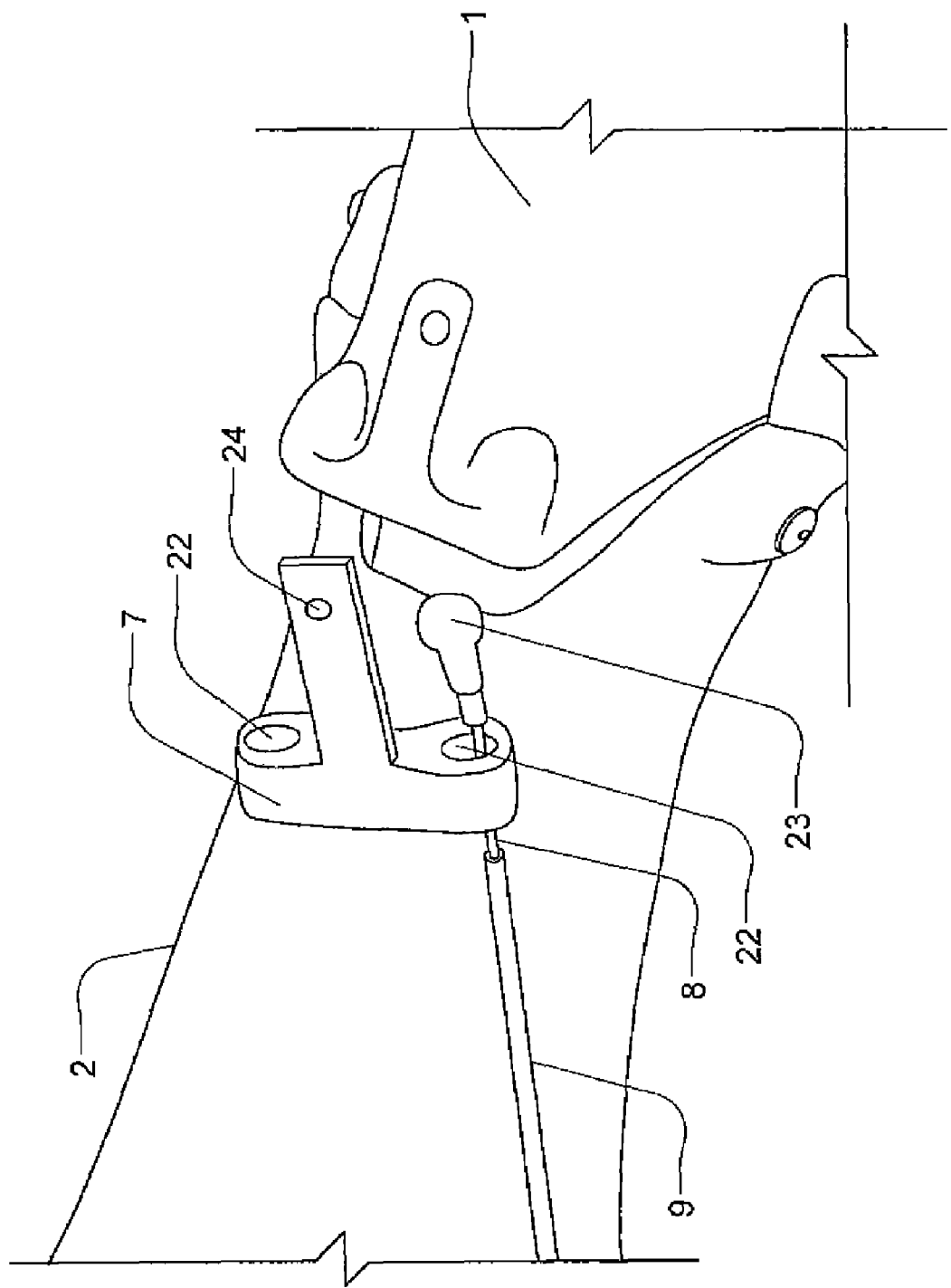
FIG. 14 is a detail view of the ankle hinge assembly of the present invention.

FIG. 14 is a detail view of the ankle hinge assembly of the present invention. In this figure, the ankle hinge assembly 4 has been removed from the heel portion of the foot plate 1 for illustrative purposes. The ankle hinge assembly 4 is preferably T-shaped and comprises two apertures 22, one on either side of the ankle hinge assembly, through which the cable 8 passes. If there is only one main hinge assembly on the device, then a cable 8 will pass through only one of the apertures 22 (as shown in FIG. 14). If there are two main hinge assemblies on the device, then a cable 8 will pass through both of the apertures 22. The cable 8 preferably comprises a stop 23 that prevents the cable from pulling out of the ankle hinge assembly 7 when the cable is pulled taught. A third aperture 24 allows the ankle hinge assembly 7 to be anchored to the foot plate 1 by a screw when the ankle hinge assembly 7 is inserted back into the heel portion of the foot plate 1.

Although the preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A knee-ankle-foot orthotic device comprising:
   (a) a main hinge assembly;
   (b) an ankle hinge assembly;
   (c) two ankle pivot points;
   (d) a foot plate;
   (e) a lower leg housing member;
   (f) an upper leg housing member; and
   (g) a cable;
   wherein the main hinge assembly comprises a first elongated member and a second elongated member;
   wherein the first elongated member is fixedly attached to the lower leg housing member and the second elongated member is fixedly attached to the upper leg housing member;
   wherein the first elongated member comprises a gear and a unidirectional bearing;
   wherein the gear comprises teeth;
   wherein the unidirectional bearing is situated inside of the gear;
   wherein the main hinge assembly further comprises a locking lever;
   wherein the locking lever comprises teeth and a spring;
   wherein the spring maintains the locking lever in an engaged position unless the spring is compressed;
   wherein when the locking lever is in an engaged position, the teeth of the locking lever engage with the teeth on the gear, thereby maintaining the gear in a stationary position;
   wherein when the gear is maintained in a stationary position, the unidirectional bearing only allows the first and second elongated members to move in one direction in relation to one another, that direction corresponding to the extension of a patient's leg at the knee;
   wherein when the cable is pulled taught, the spring of the locking lever is compressed, and the locking lever is disengaged from the gear;
   wherein when the locking lever is disengaged from the gear, the gear allows the first and second elongated members to move in two directions in relation to one another, those two directions corresponding to the flexion and extension of a patient's leg at the knee;
   wherein the foot plate comprises a heel portion;
   wherein the ankle hinge assembly is situated above the heel portion of the foot plate; and
   wherein the cable connects the ankle hinge assembly to the locking lever.

2. The knee-ankle-foot orthotic device of claim 1, wherein when a patient wearing the device dorsiflexes his ankle, the cable is pulled taught, and the locking lever is disengaged from the gear, thereby allowing the patient to either flex or extend his leg at the knee.

3. The knee-ankle-foot orthotic device of claim 2, wherein when the patient's ankle is no longer dorsiflexed, the locking lever engages with the gear, thereby allowing the patient to extend his leg at the knee but not to flex it.

4. The knee-ankle-foot orthotic device of claim 1, wherein the foot plate, lower leg housing member and upper leg housing member are all open along the front and are comprised of a durable plastic material that is able to slightly bend.

5. The knee-ankle-foot orthotic device of claim 1, wherein the device comprises one or two main hinge assemblies;
   wherein the ankle hinge assembly comprises a first and second aperture;
   wherein for each main hinge assembly on the device, a single cable extends through one of the apertures on the ankle hinge assembly;
   wherein each cable comprises a stop that prevents the cable from exiting the ankle hinge assembly when the cable is pulled taught; and
   wherein the cable is fixedly attached to the locking lever.

6. The knee-ankle-foot orthotic device of claim 1, wherein each ankle pivot point comprises a plastic or metal hinge that joins the foot plate to the lower leg housing member at a position corresponding roughly to a patient's ankle when the patient is wearing the device.

7. The knee-ankle-foot orthotic device of claim 1, wherein the first and second elongated members are joined together with a main screw and a threaded shaft;
   wherein the main screw fits into the threaded shaft; and
   wherein the shaft extends through the center of the unidirectional bearing.

8. The knee-ankle-foot orthotic device of claim 1, wherein the second elongated member comprises two circular arms that form a channel into which the first elongated member is inserted.

9. The knee-ankle-foot orthotic device of claim 8 wherein the main hinge assembly further comprises a washer that lies between the gear and one of the circular arms of the second elongated member.

* * * * *